United States Patent [19]

Pennace et al.

[11] Patent Number: 4,818,576
[45] Date of Patent: * Apr. 4, 1989

[54] SILICONE RELEASES, LAMINATES AND METHODS

[75] Inventors: John R. Pennace, Paxton; Sharon A. Quinn, Hudson, both of Mass.

[73] Assignee: Flexcon Co., Inc., Spencer, Mass.

[ * ] Notice: The portion of the term of this patent subsequent to Sep. 30, 2003 has been disclaimed.

[21] Appl. No.: 913,122

[22] Filed: Sep. 29, 1986

Related U.S. Application Data

[63] Continuation of Ser. No. 596,767, Apr. 4, 1984, Pat. No. 4,614,677, which is a continuation-in-part of Ser. No. 405,637, Aug. 5, 1982, abandoned, which is a continuation of Ser. No. 296,701, Aug. 27, 1981, which is a continuation of Ser. No. 99,265, Feb. 20, 1980, abandoned, and a continuation of Ser. No. 58,983, Jul. 10, 1979, abandoned, and a continuation of Ser. No. 969,254, Dec. 13, 1978, abandoned, and a continuation of Ser. No. 759,154, Dec. 13, 1977, abandoned, which is a continuation-in-part of Ser. No. 558,324, Mar. 14, 1971, abandoned, which is a continuation-in-part of Ser. No. 538,588, Jan. 16, 1975, abandoned.

[51] Int. Cl.$^4$ .......................................... A61F 13/02
[52] U.S. Cl. .................................... 428/40; 428/352; 428/354; 428/355; 428/447; 427/341 B; 427/411; 427/207.1; 427/208

[58] Field of Search ................. 428/40, 352, 748, 447, 428/355, 354; 427/391, 411, 207.1, 208

[56] References Cited

U.S. PATENT DOCUMENTS

| | | | |
|---|---|---|---|
| 2,985,554 | 5/1961 | Dickard | 428/40 |
| 3,006,463 | 10/1961 | Bond et al. | 428/40 |
| 4,039,707 | 8/1977 | O'Malley | 428/40 |
| 4,258,102 | 3/1981 | Traves et al. | 428/448 |
| 4,614,677 | 9/1986 | Pennace et al. | 428/447 |

Primary Examiner—Edith Buffalow
Attorney, Agent, or Firm—George E. Kersey

[57] ABSTRACT

A silicon release laminate formed by a support with a silicone release layer. A separate pressure-sensitive silicon adhesive may be on the same or opposite side of the support as the release layer. The force required to separate the adhesive from the release layer is less than about 100 grams (3.3. oz.) per inch, and preferably less than 50 grams (1.7 oz.) per inch.

The release layer is formed from one or more polysiloxanes having a viscosity below 900 centipoises, and preferably below about 600 centipoises, with a high degree of cross-linking. The polysiloxanes may be produced directly by hydrolysis of substituted halosiloxanes and depolymerization; or by hydration of higher molecular weight polysiloxanes and heat treatment to produce lower weight constituents.

15 Claims, 4 Drawing Sheets

10

10'

10"

SILICONE RELEASES, LAMINATES AND METHODS

CROSS-REFERENCE TO RELATED APPLICATIONS

This application is a continuation of Ser. No. 596,767 filed Apr. 4, 1984, now U.S. Pat. No. 4,614,677 issued Sept. 30, 1986., a continuation-in-part of Ser. No. 405,637 filed Aug. 5, 1982, abandoned, which is in turn a continuation of Ser. No. 296,701 filed Aug. 27, 1981 that was continued from now abandoned applications Ser. Nos. 99,165 of Feb. 20, 1980; 58,983 of July 10, 1979; 969,254 of Dec. 13, 1978; 759,154 of Dec. 13, 1977; being a continuation-in-part of abandoned Ser. No. 558,324 of Mar. 14, 1971, which is a continuation-in-part of abandoned Ser. No. 538,588 of Jan. 16, 1975.

BACKGROUND OF THE INVENTION

Pressure-sensitive release and adhesive materials are well known and in wide commercial use. They secure tapes, labels, or other articles to receiving surfaces. Such adhesives can be attached to a variety of materials by simple application of pressure. Tapes coated with such adhesive on opposite sides can be used to join two articles together.

Pressure-sensitive adhesives are generally based on elastomeric polymers, including natural and synthetic rubbers. They can be compounded with extenders, plasticizers, tackifiers and other materials to provide specifically desired properties. Examples of such materials and their uses are provided in numerous U.S. patents, including U.S. Pat. Nos. 3,085,903; 3,246,049; 3,356,635; 3,501,365; and 3,532,652.

Because pressure-sensitive adhesives are tacky, it is customary to cover their exposed surfaces temporarily, and removably, with a release layer, typically a nontacky silicone polymer. This facilitates handling, storage and dispensing. The resulting products include label stock in which a support base is bonded to the adhesive and the exposed adhesive surface is covered with a silicone-release paper or film.

Another example is a spirally wound tape with a film or paper support having one surface bonded to an adhesive. The exposed adhesive surface is in contact with a release layer that is carried by the opposite side of the support, or by a separate interleaving support. Still another example is a spirally wound transfer tape in which the support is coated on both sides with release layers, and one of the release layers is overcoated with adhesive. The adhesive initially can be formed directly on the support surface, or on the release surface. The latter is necessary for transfer tapes with release coatings on both sides of the support. Consistently low uniform release forces between the adhesive and release layer are more difficult to obtain when the adhesive is solidified from a liquid in contact with the release layer surface.

The foregoing structures are "laminates" which are composite structures having at least one support, temporary or permanent, and at least one release layer in surface contact with the adhesive. Other layers such as a pressure-sensitive adhesive layer, and a second release layer or a second support may also be present.

Elastomeric, pressure-sensitive silicone adhesives are widely known and have a number of attractive properties. They are useful over a wide range of temperatures, both high and low. They are chemically stable, and have good adhesion to a variety of materials. However, silicon pressure-sensitive adhesives adhere with such tenacity to conventional release surfaces, that the materials often tear before releasing. The consequence is that the use of silicone adhesives has been limited generally to direct application without a release layer, or to use with plastic films strong enough to withstand the considerable release forces required in unwinding spiral tapes. Release surfaces with ridges which tend to reduce contact area have also been employed with limited success, but at increased expense.

Accordingly, an object of the invention is to realize a silicon pressure-sensitive release laminate that is practical for use with silicone adhesives, both immediately after preparation and after extended periods of storage. A related object is to achieve both release laminates, and release-adhesive laminates.

Another object is to realize silicon laminate structures which can be releasably separated with stripping or release forces that are comparable with known, nonsilicone pressure-sensitive release laminates.

Still another object is to realize silicone pressure-sensitive laminate structures which permit the use of existing pressure-sensitive techniques and equipment.

A further object of the invention is to facilitate the use of silicone adhesives. A related object is to provide release materials which expedite the use of such adhesives.

Still another object is to achieve release and adhesive combinations which are readily produced and are usable over a wide range of temperature conditions. A related object is to achieve a silicone release and adhesive laminate which is operable under frigid Arctic conditions, as well as humid and high temperature tropical conditions.

SUMMARY OF THE INVENTION

In accomplishing the foregoing and related objects, the invention provides a silicone release article which employs one or more releasable polysiloxanes which, before curing, have solventless viscosities in the range from about 60 centipoises to about 100 centipoises, and from about 100 centipoises to about 600 centipoises. A less preferred range of viscosities is from above about 600 centipoises to below 900 centipoises. A similarly suitable viscosity range extends below about 60 centipoises.

Silicone release resins for the practice of the invention are sold essentially as linear polymers or prepolymers in liquid form, with or without solvents. They are coated only paper, film or other supports and then cured, typically by heat and/or surface catalytic action, to form solid, nontacky, cross-linked polymers in situ.

These release resins typically are formed by hydrolysis of halosilanes or by hydration and heat treatment of polysiloxanes. They consist predominantly of repeating units of the structure

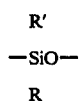

where
R is hydrogen, hydroxyl or organic radical, principally alkyl or aryl;
R' is organic;

O is oxygen; and

Si is silicon.

The degree of polymerization is sufficient to produce a linear prepolymer material with no significant cross-linkage. While liquids are preferred, high molecular weight wax-like solids can be substituted where sufficient solvent or can be employed to provide fluidity for coating without premature curing.

It is believed that suitable silicone release prepolymers are 95 percent repeating units of the above structure with reactive end groups. Small quantities of other modifying units may be present, if desired. Such release materials are described, for example, by Alvin E. Bey in "New Developments in Silicone Release Coatings for Pressure-Sensitive Adhesives", October, 1972 *Adhesives Age*, pages 29–32.

In accordance with the present invention, it has been found that silicone pressure-sensitive adhesives can be contacted with release layers formed from selected silicone release polymers, stored for extended periods, and removed for use when needed. The equipment and procedures are generally comparable to those employed with rubber and acrylic-based adhesives. These results are obtained by employing one or more silicone release polymers with a net viscosity below 900 centipoises. The polymers subsequently are highly cross-linked, as measured by the absorption of solvent. The greater the degree of cross-linking, the less is the absorption if solvent. Silicone release polymers are sufficiently cross-linked for use with the laminates of the present invention if they absorb the solvent heptane to an extent less than about 200 percent of their cured weight.

The absorption of heptane is measured using a sample of liquid coating material, catalyzed for curing. The sample is placed in a container which may be laboratory weighing dish of aluminum foil. Inert solvent, if present, is removed and the liquid fully cured. A sufficient sample provides a cured thickness of about one fourth inch. The cured sample is removed, weighed, and immersed in heptane until the sample reaches substantially constant weight. The sample is removed from the heptane, surface dried by blotting and reweighed. The increase in weight represents the amount of absorbed heptane.

When measured by the foregoing technique, conventional silicone release polymers will absorb about 600 percent or more of their original weight, and the increase in weight often continues well beyond twenty-four hours. Preferred materials according to the present invention usually attain substantially constant weight within twenty-four hours.

The release mechanism theoretically involves, as noted, for example, in Bey, cited above, a low polarity surface of low surface tension, highly flexible polymer chains, and incompatibility of the release surface with dissimilar contacting adhesive polymers. The degree of cross-linking affects the release forces. However, such theories have not led to successful release laminates for silicone pressure-sensitive adhesives.

In accordance with the present invention, it has been discovered that if the degree of cross-linking is substantially increased over prior practice, release laminates for silicone adhesives can be obtained with low release values, even though the flexibility of the release polymer is reduced and the contacting polymeric materials have substantial similarity.

A variety of chemical techniques are known for obtaining high cross-link density. For example, a high degree of functionality can be provided on a polysiloxane prepolymer, as by silicon-bonded hydrogen or vinyl substituents, which are polymerized and cross-linked with polyfunctional cross-linking agents. Additive reactions between unsaturated hydrocarbon groups, such as vinyls or the like, and silicon-bonded hydrogens are preferred. The unsaturated hydrocarbon groups may be provided as reactive groups in a hydrocarbon molecule, preferably of low molecular weight, as in Example I, or on a polysiloxane prepolymer, as in Example VI, below.

It is also preferred that all or a majority of the polysiloxane prepolymers be of low molecular weight, preferably having a Brookfield viscosity at 25 degrees Centigrade below 900 centipoises, corresponding to a molecular weight below about 25,000. Such lower molecular weight prepolymers are believed to minimize steric effects in the attainment of a highly cross-linked structure. The total liquid coating prepolymer composition, absent inert solvent, preferably has a viscosity below about 600 centipoises and most preferably less. Particularly suitable materials have a net viscosity in the range extending from 300 to between 60 and 100 centipoises. Less suitable but usable are materials having a viscosity range about 600 centipoises and below 60 centipoises.

It is preferred in some cases that the silicone release layers of the present invention be formed from reactive polysiloxane prepolymer compositions having a substantial content of silicon-bonded hydrogen substituents sufficient to provide an infra-red (IR) absorption ratio above about 0.4 for the ratio of (a) silicon hydrogen (Si-H) absorption, in the range from about 4.5 to 4.8 microns, to (b) for carbon-hydrogen (C-H) absorption in the range from about 3.0 to 3.5 microns.

Even where the absorption ratio for hydrogen-bonded silicon is below 0.4, suitable release materials can be realized if the material contains a sufficient number of other reactive groups, such as vinyls.

Prepolymers containing silicone-bonded hydrogen can comprise the major component, as in Examples I–V, below, which can be highly cross-linked with co-reactive silanes, multivinyl containing cross-linking agents, or similar reactive unsaturated compounds such as dicyclopentadiene, or, as illustrated in Example VI, the silicone-bonded, hydrogen containing prepolymer can be employed to cross-link other co-reactive polysiloxane prepolymers having sufficient co-reactive substituents, preferably vinyl groups, to provide a siloxane copolymer with a high degree of cross-linking. Catalysts for the above reactions are known and are exemplified in the Examples.

DESCRIPTION OF THE DRAWINGS

In the accompanying drawings:

FIG. 9D is a schematic diagram of a further laminate in accordance with the invention.

DETAILED DESCRIPTION

Detailed considerations applicable to the practice of the invention are set forth below.

(a) Absorption Spectra

Figure 1:
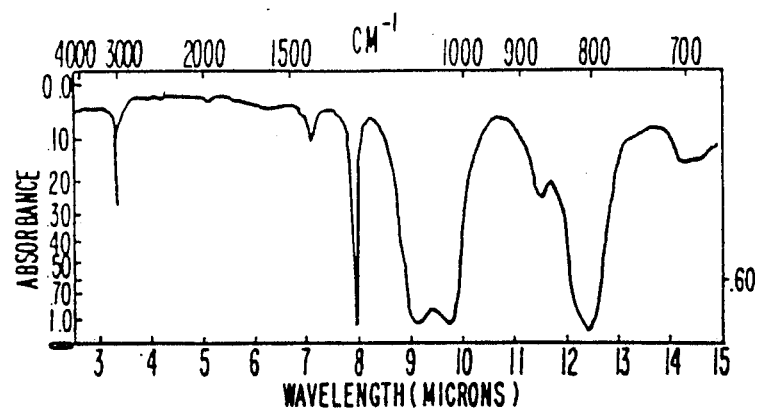
FIG. 1 is an infrared (IR) spectrographic absorption chart for silicone release resin prepolymer No. 4280 of the General Electric Company.
Figure 2:
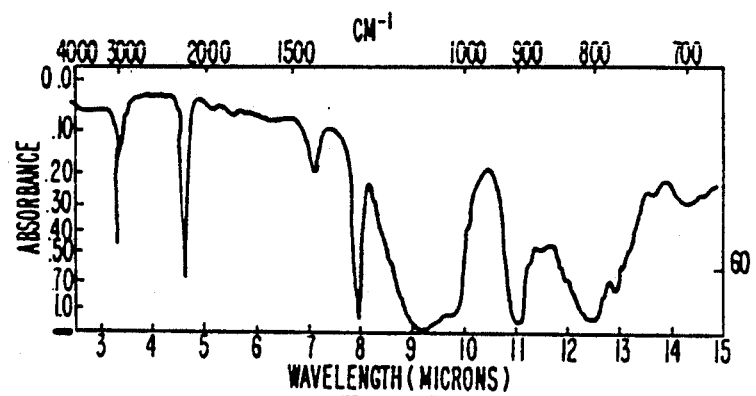
FIG. 2 is an IR spectrographic absorption chart for silicone release resin prepolymer No. SS4281C of the General Electric Company.
Figure 3:
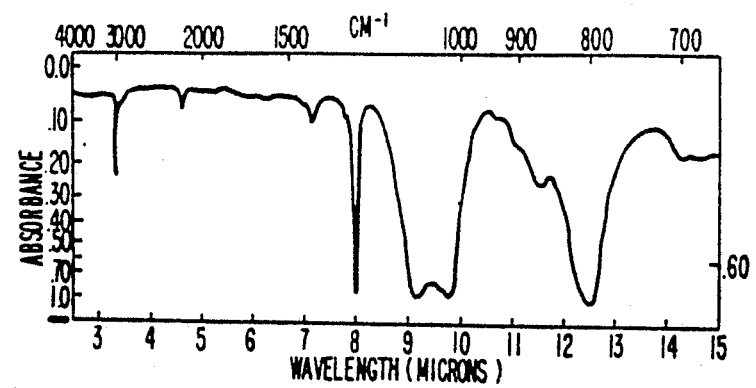
FIG. 3 is an IR spectrographic absorption chart for silicone release resin prepolymer No. 4191 of the General Electric Company.
Figure 4:
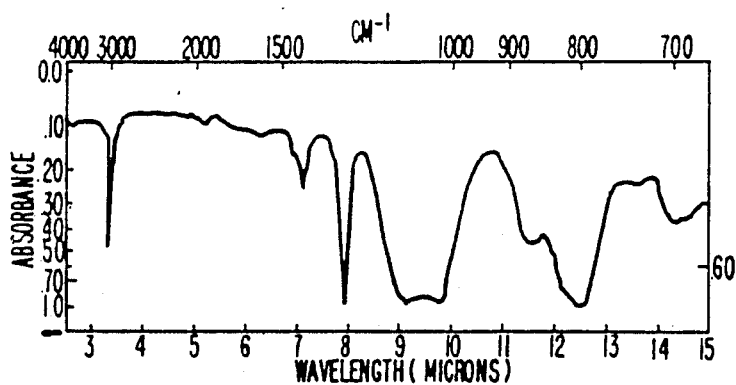
FIG. 4 is an IR spectrographic absorption chart for silicone release resin prepolymer No. X2-7018 of the Dow Corning Corporation.
Figure 5:
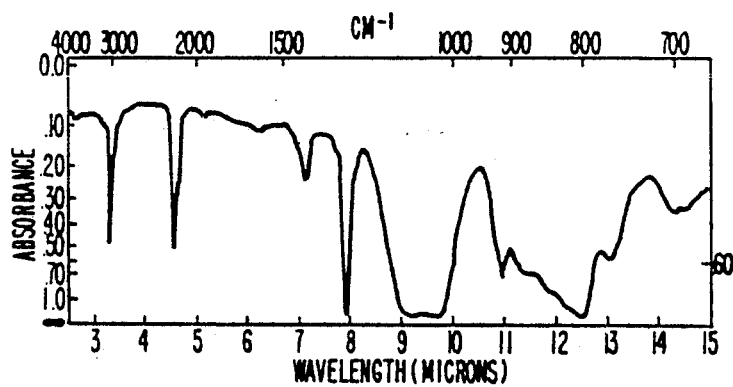
FIG. 5 is an IR spectrographic absorption chart for silicone release resin prepolymer No. X2-7016 of the Dow Corning Corporation.
Figure 6:
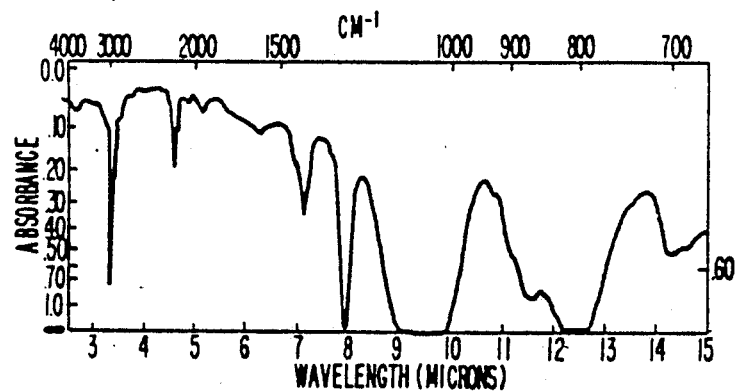
FIG. 6 is an IR spectrographic absorption chart for silicone release resin prepolymer No. 23/30 of the Dow Corning Corporation.

The absorption spectra of FIGS. 1–8 were obtained by placing a cast film, free of solvent, in or on a sodium chloride capillary cell or plate. Cells were used for lower viscosity materials where too little material was retained on a plate (FIGS. 2, 4, 5 and 7). Plates were used for higher viscosity materials (FIGS. 1, 3 and 6). The runs were performed on an INFRACORD prism IR spectrophotometer. The cast film was of a thickness such that both absorption peaks of interest, when present, fell within about the absorption region extending from above 0.2 to 0.7.

The determination of the ratio of absorption in the range from 4.5 to 4.8 microns for silicon-bonded hydrogen (SiH), to the absorption in the range from 3.0 to 3.5 microns for the carbon-bonded hydrogen (CH) is illustrated with respect to FIG. 7 as follows:

(a) The first absorption peak is 0.72 at 3.4 microns. The estimated base line at 3.4 microns is about 0.05 (by straight line extrapolation across the absorption interval indicated by the broken line).

(b) The absorption at 3.4 microns for (CH), was therefore determined to be about 0.67 (0.72 minus 0.05).

(c) Similarly, the second absorption peak was 0.29 at 4.6 microns. The absorption (SiH), adjusted for base line was determined as 0.275 (0.29 minus 0.015).

(d) The ratio (IR), therefore was 0.41 (obtained from dividing 0.275 by 0.67). (IR=(SiH)/(CH). IR ratios from FIGS. 1–8 were calculated as indicated above and are listed in the following TABLE I.

TABLE I

| | (IR Ratios) | | |
|---|---|---|---|
| FIG. | Numerator (SiH) Absorption (4.5–4.8) | Denominator (CH) Absorption (3.0–3.5) | SiH/CH Absorption Ratio |
| 1 | — | 0.19 | — |
| 2 | 0.65 | 0.43 | 1.51 |
| 3 | 0.05 | 0.20 | 0.25 |
| 4 | — | 0.47 | — |
| 5 | 0.34 | 0.43 | 1.03 |
| 6 | 0.17 | 0.72 | 0.24 |
| 7 | 0.27 | 0.67 | 0.41 |
| 8 | 0.13 | 0.57 | 0.23 |

As sold commercially and recommended for use by the suppliers, the prepolymers of FIGS. 1 and 2, and also of FIGS. 4 and 5, are mixed in the proportion of 10 parts by weight of the first material to 1 part by weight of the second material and coated with or without solvent, and cured. They form release layers, but not for silicone adhesives.

The materials of FIGS. 3 and 6 are conventional solvent coating release materials, cured with catalyst and small quantities of reactive silanes as recommended by the suppliers.

Figure 7:
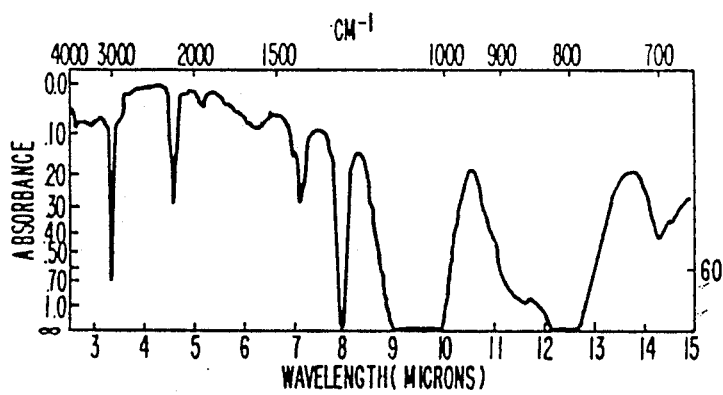
FIG. 7 is an IR spectrographic absorption chart for silicone release resin prepolymer No. EP 6396 of the Imperial Chemical Industries, Ltd., Stevenston, Ayrshire, Scotland.

The material of FIG. 7 is a solventless coating material cured with added platinic acid catalyst containing dicyclopentadiene, as recommended by the supplier.

When such materials are coated on densified release paper, cured, and laminated to conventional rubber or acrylic-based pressure-sensitive adhesives, suitably stable release forces are generally obtained for solvent applied release layers in the range of 16 to 40 grams per inch of width at slow speed, and 40 to 100 grams per inch of width at high speed, measured as more fully explained in Example 1 below.

The coatings applied without solvents generally give about one-half these values. However, when laminated to silicone-based pressure-sensitive adhesives, especially after a few days of storage, conventional release sheets often tear before release is obtained. Also, the tack or adhesion of the silicone adhesives is sometimes diminished, believed to be due to retention of release polymer on the surface of the adhesive.

Figure 8A:
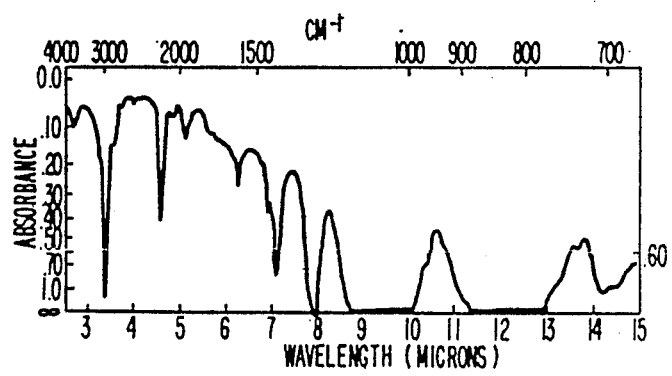
FIG. 8A is an IR spectrographic absorption chart for Dow Corning Q-2-7044/7045.
Figure 8B:
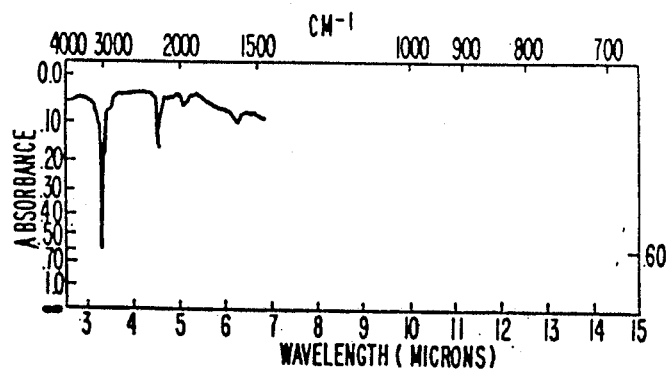
FIG. 8B is a reduced portion of FIG. 8A to permit determination of the IR ratio.

In the case of FIG. 8, although the absorption ratio of silicone-bonded hydrogen is low (less than 0.40), there are compensating vinyl reactive groups which make use of material suitable for the practice of the invention.

(c) Preferred Embodiments of the Invention

The invention is illustrated by the following non-limiting examples:

EXAMPLE I

A carrier was provided by a conventional 42-pound per ream (250,000 square inches) super calendered and densified Kraft release paper and coated as follows:

A silicone-release polymer EP 6396 from Imperial Chemical Industries Limited (ICI), Ayrshire, Scotland was mixed with ICI catalyst EP 6439 (platinic acid type containing dicyclopentadiene in the weight ratio of 1.5 parts catalyst to 100 parts resin and placed in the pan of an offset gravure coating apparatus. EP 6396 is believed to be predominantly silanol terminated polydimethylsiloxane having a viscosity of 60 to 100 centipoises at 25 degrees C., in combination with a minor proportion of polymethylhydrogensiloxane having a viscosity of about 25 centipoises at 25 degrees C. The net viscosity is about 70 centipoises and is verifiable from the IR spectrographic absoprtion chart of FIG. 7. In addition, FIG. 7 and Table I show that the material has a sufficient amount of hydrogen-bonded silicone (IR ratio of 0.45) to provide an adequate release.

A gravure roll, partiallyimmersed in the pan, with 150 lines per inch engraved on steel was employed with a rubber transfer roll operated at a roll speed ratio of 1:1. The release carrier paper was fed over the transfer roll by a steel drive roll, with the paper fed between the nip formed by the rubber transfer roll and the steel drive roll, at a speed six times as great as the linear speed of the surface of the transfer roll surface. This provided a smooth, uniform coating of about 0.3 pounds coating per ream. The coating was then passed into a hot air oven and cured for 7 seconds at 395 degrees F. (202 degrees C.). The second or reverse side was then similarly coated and cured, with the first side again heated for 7 seconds at 395 degrees F. (202 degrees C.).

The result was a silicone release article suitable for use with a wide variety of adhesives, including silicone adhesives.

EXAMPLE II

The release paper of Example I was further coated on the first, twice heated side, by drawing the paper under a shimmed steel bar with 1.0 to 1.5 mils thickness of silicone pressure-sensitive adhesive (after drying and curing). The adhesive employed was SR 574 obtained from the General Electric Company and catalyzed as recommended with 1.5 percent by weight of equal weight parts of dichlorobenzoyl peroxide and silicone oil or dibutyl phthalate. The coating was cured at 300 degrees F. for 2 minutes. The cured adhesive was covered with a 0.002 inch thick strip of Mylar polyester film and a compressive force of about 400 pounds per inch applied for eight minutes.

It is to be noted that the composition for SR 574 adhesive is disclosed by William J. O'Malley in an article titled "Silicone Pressure Sensitive Adhesives for Flexible Printed Circuits", Apr. 24, 1974, prepared for a meeting of the Multilayer Committee of the Institute of Printed Circuits. The specific composition of SR 574 is discussed, for example, on page 1 at line 8 and in FIGS. 1 and 2. It is indicated that pressure-sensitive adhesives of the SR 574 type are based on the combination of a gum and an "MQ" resin. The gum component, as shown by FIG. 1 of the article, is a polysiloxane gum such as methylphenylpolysiloxane. FIG. 2 of the article discloses the MQ resin to be an organopolysiloxane resin.

The result was a suitable silicone-adhesive release article.

EXAMPLE III

The adhesive of Example II is substituted by an organopolysiloxane pressure-sensitive adhesive as specifically set forth in U.S. Pat. No. 2,857,356 to Goodwin, Jr., which teaches that specific resins (column 4, beginning at line 15) are reacted with linear, high-viscosity organopolysiloxane fluids (column 4, beginning at line 47).

EXAMPLE IV

The slow speed release between the silicone adhesive of Examples I–III and the silicone release surface is measured with an Instron tester, Model TM. In the slow speed test, a sample 1.2 inch wide by six inches in length is stripped at 90 degrees and 12 inches per minute and the release measured. This procedure is a modification of TLMI Adhesion Test No. VII-LD. In the modified procedure the sample to be tested is secured to a rigid plate using two-sided adhesive tape, with both release layer and its carrier exposed. Removal of release layer is initiated, and the sample is clamped in the jaws of the tester.

For high speed stripping, the test was conducted on a TLMI tester, and samples 1 inch by 6 inches were stripped at 180 degrees and 600 inches per minute, following TLMI release test method VIII-LD270. In one test the measured stripping or release forces were as follows, for various periods of storage time at standard conditions of temperature and pressure following preparation of the laminate:

| Storage Interval | Low Speed Release Force | High Speed Release Force |
| --- | --- | --- |
| Zero | 9–16 grams | 25–30 grams |
| 24 hours | 14–24 grams | 25–30 grams |
| 1 week | 15–25 grams | 25–30 grams |

EXAMPLE V

Ten grams of ICI release prepolymer EP 6396 was dissolved in 87 grams of heptane. To this solution was added one (1.0) c.c. of a 50 percent by weight solution of triacetoxy methyl silane in toluene, and 0.5 grams of di-N-butyl tin dioctoate, a known slicone catalyst.

The resulting release mixture was coated using a Number 4 Mayer rod onto a support film of Mylar polyester, dried and cured in an oven for 20 seconds at 275 degrees F. When overcoated with General Electric SR 574 silicone pressure-sensitive adhesive, laminated and tested, all as set forth in Example IV, low release values immediately and after storage for one week were obtained.

When the release mixture was coated on untreated paper low release values were not obtained. However, if the paper is provided with a suitable barrier coating, e.g. a conventional cured silicone release coating such as the materials of FIG. 3 or 6, paper can be used as the support.

EXAMPLE VI

General Electric experimental pressure-sensitive adhesive No. 404-333 was substituted for adhesive SR 574 in Example I. The resulting material was laminated and tested as in Example IV. Similar release values were obtained.

EXAMPLE VII

The prepolymer of FIG. 2, having a comparatively high IR absorption ratio (of 1.51 as shown in Table I) and a viscosity of 600 centipoises, is used after being suitably cured with catalyst such as that of Example I. The viscosity of 600 centipoises is verifiable from literature supplied by the manufacturer. Improved release properties for silicone adhesives are obtained.

EXAMPLE VIII

The prepolymer of FIG. V also having a comparatively high IR absorption ratio (of 1.03 as shown by Table I) and a viscosity believed to be below 900 centipoises is used when suitably cured with a catalyst such as that of Example I. The low viscosity below 900 centipoises is supported by the suitability of the material for reverse roll coating. Improved release properties for silicone adhesives are obtained.

EXAMPLE IX

A mixture of one part by weight Q-2-7045 was mixed with ten parts Q-2-7044, obtained from the Dow Corning Corporation. The mixture was substituted for the ICI material specified in Example I.

Q-2-7044 is understood to be a polysiloxane having a plurality of reactive vinyl substituents attached to its silicone atoms, a viscosity of about 300 centipoises, and a molecular weight of about 15,000, corresponding to a degree of polymerization of about 200. It also contains rhodium, or platinum-based catalyst.

Q-2-7045 is understood to be approximately 60 percent by weight Q-2-7044 and 4 percent by weight polymethylhydrogensiloxane of low molecular weight. This material is understood to have a degree of polymerization of about 40 units and an IR ratio substantially greater than 0.4. The reaction hydrogen substituents of the Q-2-7045 cross-link with the vinyl groups of the Q-2-7044 prepolymer.

The material was coated, cured, and tested in accordance with Example IV, except that the rubber transfer roll and the steel drive roll were driven at the same speed. This was greater than the surface speed of the gravure roll by 10 percent or more. A coating weight of between one and two pounds per ream was applied.

Although this material has a comparatively low absorption ratio (of 0.20 as indicated in Table I) it has a sufficient number of reactive vinyls to provide a suitable release.

Similar results were obtained as for Examples I and II. In addition this release material was employed on the Alaska pipeline and found to be the only material, of those tested, that could be used successfully under Arctic conditions.

(d) Summary of the Examples)

Of the foregoing Examples I, II, VI, VII, and IX are preferred. Assurance of the suitability of the material is made by choosing relatively low viscosity material below 900 centipoises at 25 degrees C., and preferably lower, with a sufficient number of reactive groups, either at or intermediate terminal positions. In the case of reactive hydrogen an indicator of suitability is given by a relatively high IR ratio (above 0.4). Other indices of active sites are employed for vinyls, alkoxys, esters and the like.

(e) Preferred Adhesives

It is also preferred to use a pressure-sensitive silicone adhesive containing an appreciable number of essentially inert substituents other than methyl, for example phenyl groups, as disclosed, for example, in U.S. Pat. Nos. 2,857,356 and 3,839,075. Such groups may be provided, for example, by incorporating phenylmethyl siloxane in the polymer monomer units. Inclusion of "M" and "Q" units as described in the above patents is also preferred. The amount of such "M" and "Q" units can be varied to vary the tack of the resulting adhesives.

It will be appreciated that other organopolysiloxane adhesives may be used as well.

(f) Laminates According to the Invention

Figure 9A:
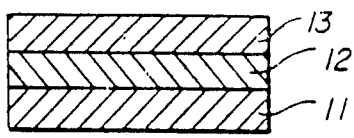
FIG. 9A is a schematic diagram of a release laminate in accordance with the invention.
Figure 9B:
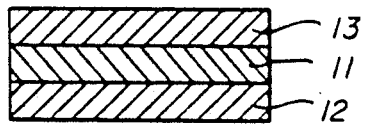
FIG. 9B is a schematic diagram of a release-adhesive laminate in accordance with the invention.

For each of the above Examples, the initial laminates were in accordance with FIG. 9A. Each such laminate 10 consisted of a support layer 11 of paper, and a cured, highly cross-linked silicone release polymer 12 on the support layer 11. This is followed, as shown in FIG. 9B, by a silicone pressure-sensitive adhesive layer 13 adhered to one surface of a Mylar film 14. The layer 12 is removably adhered upon the adhesive layer 13; and the release paper carrier 11 adhered to the release layer 12 on the side opposite the adhesive 13. The adhesive can be readily stored, handled, dispensed and applied in this form.

To form a spirally-wound tape 10' as illustrated in FIG. 8C, the silicone release layer 12 is applied to the side of the Mylar film 14 opposite the adhesive 13 and no separate carrier sheet is needed.

Figure 9C:
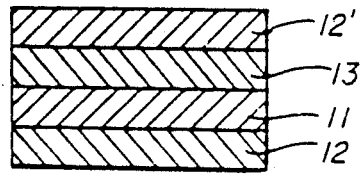
FIG. 9C is a schematic diagram of another laminate in accordance with the invention.

For the transfer tape 10" as illustrated in FIG. 9C, both sides of the Mylar 14 or other support are coated with respective release layers 12 and 12'. It should be noted that low release values were obtained even though the adhesive 13 was applied and cured directly on the release surface.

(g) Cross-Linking Considerations

Each of the foregoing Examples provides a high degree of cross-linking. In all cases, polysiloxane prepolymers with a plurality of silicone-bonded hydrogen substituents were cross-linked with compounds having a plurality of vinyl, hydroxyl or esteryl groups that are co-reactive with the hydrogen substituents. The prepolymers are believed to have substantially the following structure:

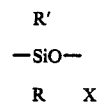

where
R' is an alkyl, preferably methyl, radical;
R is partially or entirely hydrogen and the balance if any, is an alkyl, preferably lower carbon chain radical;
O is oxygen;
Si is silicon; and
X is below about 350 and preferably less.

Such low molecular weight materials provide a Brookfield viscosity at 25 degrees C. below 900 centipoises, and/or preferably less. These prepolymers are believed to be substantially homopolymers of methylhydrogenpolysiloxane when X is about 40; or are copolymers with dimethylpolysiloxane when X is greater than 40 and below about 350 and preferably below about 300.

The above prepolymers, suitably catalyzed, are copolymerized and highly cross-linked by materials having a plurality of groups that are co-reactive with the hydrogen substituents. Table III, below, summarizes the cross-linking materials employed in the Examples:

TABLE III

| Cross-linker | Examples |
| --- | --- |
| (1) disilanol terminated | I, V, VI, VII and VIII |
| (2) dicyclopentadiene | I, VI, VII and VIII |
| (3) methyl-triacetoxy silane | V |
| (4) polysiloxane prepolymers having a plurality of vinyl substituents | IX |

The organopolysiloxanes of Example IX and Table III (4), above, are believed to have substantially the following formula:

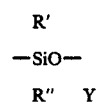

where
R' is an alkyl, principally methyl radical;
R" is a mixture of vinyl and lower alkyl groups;
O is oxygen;
Si is silicon; and
Y is below about 350 and preferably below 30.

Organosiloxanes should comprise the major portion of the coating composition. Where hydrocarbon cross-linking agents such as dicyclopentadiene are used, they preferably have small structures and are used in limited amounts sufficient to provide highly cross-linked organosilicone.

Where co-reactive polysiloxane prepolymers are employed, the ratio may vary considerably provided sufficient quantities of each reactive group are employed to produce a dense, highly cross-linked silicone. Thus in Example IX a minor portion of a silicone-bonded hydrogen-containing prepolymer is employed with a substantial number of reactive hydrogen substituents. Undue stoichiometric excess of unreacted silicon-bonded hydrogen substituents is preferbly avoided.

It is also known that hydroxyl and alkoxy groups are co-reactive with silicone-bonded hydrogen polysiloxane substituents.

(h) Cure Considerations

Cure of the release coatings should be carried substantially to completion, so that low release values are obtained. A minimum of free reactive groups at the surface is considered desirable. Substantially complete cure can be achieved using sufficient heat and time, e.g. from about 7 to about 20 seconds at 395 degrees F. or higher. Infra-red heaters can be employed usefully at the end of the cure cycle, for example to raise th coating temperature momentarily to about 500 degrees F.

(i) Conversion of Surface Reactive Groups

Where initial release values are too high, improvement can sometimes be provided by chemically converting free surface reactive groups to more inert groups. For example, free surface Si-H groups may be treated with hydrogen free, reactive silanes such as by a gas phase exposure to a mixture of trichloromethylsilane and dichlorodimethylsilane for 5 seconds at 225 degrees F., or a liquid treatment with a 3 percent by weight solution of trimethoxymethylsilane in heptane, with di-N-butyl tin diacetate as catalyst, followed by drying. Curing with sufficient heat is desirable.

Control of moisture during cure may also be important in obtaining low release values, especially for low coating weights. Ambient moisture in the drying and curing air has not been a problem and reasonable care in excluding contamination or condensation of water in the coating prepolymer mixture is sufficient. However, excess moisture in the carrier paper, where used, can be troublesome, and it is preferred that the paper have a moisture content by weight of about 4 percent or less. Pre-drying can be employed, if necessary.

(j) Coating Techniques

Good coating technique is desirable, with sufficient coating material applied to obtain a smooth uniform surface with preferably between about 0.2 and 2.0 pounds of cured release coating per ream. Coating weights between about 1.0 and 2.0 pounds per ream are preferred. These coating weights are used for normal support having good hold-out surfaces. Higher amounts may be required when the liquid release materials are applied to more porous surfaces to compensate for absorption into the support.

High speed release forces are often more important than low speed release because of the common use of high speed applicating equipment. High speed release forces less than about 100 grams (3.3 ozs.) per inch of width are preferred, forces less than about 50 grams (1.7 ozs.) are more preferred, and about 25 grams (0.8 oz.) or less per inch of width are most preferred. Such low values have not been obtainable previously in consistent commercial practice prior to the present invention, especially where the adhesive coating is formed directly on the release surface. Low release values are particularly important where paper is used as a carrier due to its limited strength, and where high speed applicating equipment is used.

(k) Sources of Release Polymers

The release polymers used in the Examples were obtained from the commercial sources indicated. Other release polymers of suitable viscosity and absorbance can be produced by hydrolysis of organo substituted halosilanes. This results in a hydrolyzate of linear and cyclic polysiloxanes. The hydrolyzate is treated with a catalyst, such as potassium hydroxide, to bring about depolymerization. The desired polymers are separated by distillation.

Suitable organopolysiloxane can also be produced by hydration of high order organopolysiloxanes and heating. This causes the high order organopolysiloxane to break into low order materials. For example, an organopolysiloxane with a viscosity of 1,000,000 centipoises at 25 degrees C. may be heated at 160 degrees C. with 1.0 percent by weight water for 2 hours to reduce the material to chains having viscosities below 1000 centipoises.

It will be understood that the foregoing description is for illustration only and that the invention includes all modifications and equivalents within the scope of the appended claims.

We claim:

1. A silicone release article comprising a backing and a releasable polysiloxane on said backing;
said polysiloxane having a viscosity before curing in the range from about 60 to below 900 centipoises at 25 degrees C. and the following structure:

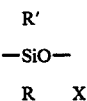

where
R' is an organic radical;
R is partially or entirely hydrogen, partially or entirely hydroxyl, and/or partially or entirely organic;
X is below 350.

2. An article as defined in claim 1 wherein an adhesive comprising an organopolysiloxane is positioned on said backing.

3. An article as defined in claim 2 wherein the releasable polysiloxane contains vinyl groups prior to curing, which can be a part of alkylvinylsiloxy groups.

4. An article as defined in claim 1 wherein the releasable polysiloxane contains reactive hydrogen prior to curing.

5. An article as defined in claim 4 wherein the reactive hydrogens are a part of alkylhydrogensilanol groups.

6. An article as defined in claim 1 wherein the releasable polysiloxane is dimethylpolysiloxane cured into a dense polymer.

7. An article as defined in claim 1 wherein said releasable polysiloxane, before curing, is formed from a plurality of prepolymers having a viscosity below 1000 centipoises.

8. An article comprising a backing with a polysiloxane adhesive and a releasable polysiloxane having:
an absorption ratio for hydrogen-bonded silicone greater than 0.4;

a solventless viscosity before curing in the range from about 60 centipoises to about 900 centipoises at 25 degrees C.; and the following structure:

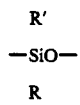

wherein
R' is an organic radical;
R is partially or entirely hydrogen, partially or entirely hydroxyl, and/or partially or entirely organic.

9. An article as defined in claim 1 wherein said releasable organopolysiloxsane layer is cross-linked to absorb less than 200 percent of its cured weight in solvent.

10. The method of producing the article of claim 1 comprising the steps of
  (a) coating the releasable polysiloxane on said backing; and
  (b) curing said releasable polysiloxane on said backing.

11. The method of producing the article of claim 1 comprising the steps of
  (a) coating the releasable polysiloxane on said backing;
  (b) curing said releasable polysiloxane on said backing;
  (c) applying an organopolysiloxane pressure-sensitive adhesive directly to said backing or upon said releasable polysiloxane; and
  (d) curing said adhesive on said backing.

12. The method of claim 10 further including the step of converting residual surface reactive groups to more inert groups.

13. The method of claim 12 wherein the surface groups are treated with hydrogen-free, reactive silanes.

14. The method of claim 10 wherein a catalyst is used selected from the class consisting of
  (a) di-N-butyltindiesters;
  (b) rhodium complexes; and
  (c) platinum complexes.

15. The method of claim 10 wherein a cross-linker is used selected from the class consisting of
  (a) dicyclopentadiene
  (b) methyltriacetoxysilane
  (c) polysiloxanes with a plurality of vinyl substituents;
  (d) disilanol terminated dimethylpolysiloxanes.

* * * * *